United States Patent [19]

Miyasaka et al.

[11] Patent Number: 4,513,138
[45] Date of Patent: Apr. 23, 1985

[54] CAMPTOTHECIN-1-OXIDE DERIVATIVES

[75] Inventors: Tadashi Miyasaka, Kanagawa; Seigo Sawada, Tokyo; Kenichiro Nokata, Tokyo; Masahiko Mutai, Tokyo, all of Japan

[73] Assignee: Kabushiki Kaisha Yakult Honsha, Tokyo, Japan

[21] Appl. No.: 414,528

[22] Filed: Sep. 2, 1982

[30] Foreign Application Priority Data

Sep. 4, 1981 [JP] Japan .................. 56-138412

[51] Int. Cl.³ .................. C07D 491/22; A61K 31/47
[52] U.S. Cl. ........................................ 546/48
[58] Field of Search .......................... 546/48

[56] References Cited

FOREIGN PATENT DOCUMENTS 0056692  7/1982  European Pat. Off.
3026172  2/1981  Fed. Rep. of Germany
116015   7/1982  Japan

OTHER PUBLICATIONS

Lown, et al., Biochemical Pharmacology, vol. 29, No. 6, pp. 905–915, (1980).
Miyasaka, et al., Heyerocycles, vol. 16, No. 10, 1713–1717, (1981).
Boekelheide, et al., J. Am. Chem. Soc., vol. 76, pp. 1286–1291, (1954).
Herz, et al., J. Am. Chem. Soc., vol. 76, pp. 4184–4185, (1954).

Primary Examiner—Donald G. Daus
Assistant Examiner—Diana G. Rivers
Attorney, Agent, or Firm—Birch, Stewart, Kolasch & Birch

[57] ABSTRACT

New 5- and/or 7-substituted camptothecin-1-oxide derivatives possessing anti-tumor activity with slight toxicity, represented by the general formula:

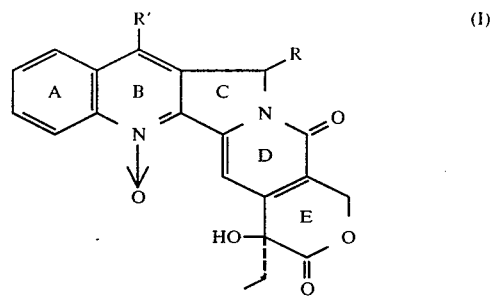

wherein R is a hydrogen atom, an alkyl group, a hydroxyl group, an alkoxy group or an acyloxy group and R' is a hydrogen atom, an alkyl group, an aralkyl group, a hydroxymethyl group, an acyloxymethyl group or a carboxymethyl group, with the proviso that both of R and R' should not be hydrogen atoms. These 5- and/or 7-substituted camptothecin-1-oxide derivatives are prepared by treating the corresponding 5- and/or 7-substituted camptothecins with a peroxidant as an N-oxidizing reagent.

8 Claims, No Drawings

CAMPTOTHECIN-1-OXIDE DERIVATIVES

BACKGROUND OF THE INVENTION

1. Field of the Invention

This invention relates to new camptothecin-1-oxide derivatives possessing anti-tumor activity (including carcinostatic activity) and to processes for the preparation of such derivatives. More particularly, this invention relates to new 5- and/or 7-substituted camptothecin derivatives carrying an oxido group in the 1-position thereof and possessing anti-tumor activity with a low level of toxicity as well as processes for the preparation of such new camptothecin derivatives.

2. Description of the Prior Art

Camptothecin is a cytotoxic alkaloid isolated from leaves and barks of Camptotheca accuminata (Nyssaceae), a plant native to China, which has a pentacyclic structure consisting of a characteristic fused 5-ring system of quinoline (rings A and B), pyrroline (ring C), α-pyridone (ring D) and a six-membered lactone (ring E) and is distinguished by displaying a strong inhibitory activity toward biosynthesis of nucleic acid. In addition, camptothecin is a unique anti-tumor substance characterized by its rapid and reversible action and its lack of any cross-tolerance with the existing anti-tumor agents and by exhibiting a strong anti-tumor activity against experimentally transplanted carcinoma such as leukemia L-1210 in mice or Walker 256 tumor in rats. Although camptothecin is still regarded as one of the most potent substances possessing anti-tumor activity, the use of this compound itself for clinical treatments is significantly limited because of high toxicity.

Accordingly, a number of attempts have been made to reduce the toxicity of camptothecin while maintaining its anti-tumor activity by converting camptothecin chemically into its derivatives. The chemical modifications so far reported mainly concern the rings D and/or E of camptothecin, but the results of such modifications revealed only failure in maintaining expected anti-tumor activity and poor improvement in toxicity [J. Med. Chem., 19 (1976), 675]. From the chemotherapeutic point of view, therefore, it is of importance that the chemical modifications of camptothecin should be restricted in the rings A, B and C without effecting any change in the rings D and E which are conceivable to be one of the essential structural elements for the expression of the above mentioned characteristic biological activities.

Except for a method for functionalizing the 12-position of camptothecin reported in 1976 which comprises a series of troublesome conversion and purification operations starting with nitration at the 12-position [P. Pei-chuang et al., Hau Hsueh Hsueh Pao Vol. 33 (1975), 719; Chem. Abstr. 84 (1976) 115629p], however, no success was reported until 1979 in connection with chemical functionalization of camptothecin in a moiety involving the rings A, B and C. This is probably ascribable to the reasons that camptothecin itself is only sparingly soluble in various organic solvents and that camptothecin possessing the nature of heterocyclic rings in its molecule is resistant to the so-called electrophilic reactions conventionally carried out on aromatic rings. In the present status, such obstacles strongly discourage chemical modifications of camptothecin contemplated intellectually for preparing new classes of derivatives thereof.

Under the above mentioned circumstances, the present inventors previously found together with co-workers processes for preparing 5- and 7-substituted camptothecins (U.S. Pat. No. 4,399,282) by introducing (1) hydroxymethyl group into 7-position of camptothecin by subjecting camptothecin to a radical reaction with methanol by the aid of sulfuric acid and a peroxide (such as potassium persulfate, sodium persulfate, ammonium persulfate, hydrogen peroxide or a tertiarybutyl peroxide) wherein the reaction is carried out usually by dissolving camptothecin in an aqueous solution of methanol-sulfuric acid, adding thereto a peroxide as a radical reaction initiator (Japanese Laid-open Patent Appln. No. 56-12391), (2) hydroxy group into 5-position of camptothecin by treating camptothecin with sulfuric acid, water and a persulfate (such as sodium persulfate, potassium persulfate and ammonium persulfate) in the presence of a metal ion (such as silver salts such as silver nitrate, silver sulfate, silver carbonate or silver acetate or a ferrous salt such as ferrous sulfate, ferrous chloride and ferrous oxide) under heat and agitation (Japanese Laid-open Patent Appln. No. 56-12392), and (3) an alkyl or aralkyl group into 7-position of camptothecin efficiently in a single step by subjecting camptothecin to a radical reaction with a compound of the general formula: RX (wherein R stands for an alkyl group or an aralkyl group, and X for —CH$_2$OH, —COOH, —CHO, —CO—R or

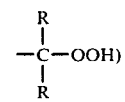

preferably in a large excess amount by the aid of sulfuric acid, water and a peroxide (such as hydrogen peroxide or tert-butylhydroperoxide) in the presence of a metal ion (such as ferrous sulfate, ferrous chloride or ferrous oxide) usually under ice-cooling and agitation and thereafter stirring while warming the mixture to room temperature (Japanese Laid-open Patent Appln. No. 56-158786). Further, the present inventors prepared together with co-workers a great number of new camptothecin derivatives possessing anti-tumor activity with slight toxicity from these 5- and 7-substituted camptothecin derivatives (U.S. Pat. Nos. 4,399,276 and 4,399,282) according to the process wherein 7-hydroxymethylcamptothecin is acylated with an acylating agent usually capable of acylating hydroxy group, for example, a halide of a carboxylic acid (such as formic acid, acetic acid, propionic acid, butyric acid, phenylacetic acid, succinic acid, trifluoroacetic acid or the like aliphatic carboxylic acid or benzoic acid or the like aromatic carboxylic acid) or a carboxylic acid anhydride whereby the hydroxy group or groups of the camptothecin is acylated to obtain 7-acyloxymethylcamptothecins or 20-O-acyl-7-acyloxymethylcamptothecins or wherein 7-hydroxymethylcamptothecin is oxidized with an oxidizing agent usually capable of oxidizing hydroxymethyl group to carboxy group, for example, an anhydrous chromate, a bichromate or a permanganate whereby 7-carboxycamptothecin is obtained, which is then esterified according to a usual manner with an alcohol (such as methanol, ethanol, propanol or butanol) to obtain 7-alkoxycarbonylcamptothecins (Japanese Laid-open Patent Appln. No. 56-12393), the process wherein 5-alkoxycamptothecins are obtained by dissolving 5-hydroxycamptothecin in a lower alcohol (such as methanol, ethanol, propanol or butanol), adding thereto an acid (such as hydrochloric acid, sulfuric acid or boron fluoride etherate) as catalyst, and heating the mixture, or wherein 5-acyloxycamptothecins or 20-O-acyl-5-acyloxycamptothecins are obtained by acylating 5-hydroxycamptothecin with a reactive acid derivative such as a halide of a carboxylic acid (such as formic acid, acetic acid, propionic acid, butyric acid, phenylacetic acid, succinic acid or trifluoroacetic acid or benzoic acid) or an acid ahydride (Japanese Laid-open Patent Appln. No. 56-12394), the process wherein camptothecin-7-aldehyde is obtained directly from the 7-hydroxymethylcamptothecin by treating the 7-hydroxymethylcamptothecin with various cationoid reagents without using any oxidizing agent [The cationoid reagent includes a variety of mineral acids (such as sulfuric acid, hydrochloric acid, perchloric acid, hydrobromic acid and the like), organic acids (such as acetic acid, propionic acid, benzoic acid, monochloroacetic acid, trifluoroacetic acid, p-toluenesulfonic acid and methanesulfonic acid), Lewis acids (such as boron trifluoride-ether, aluminum chloride and stannic chloride), organic acid halides (such as p-toluenesulfonyl chloride, phenylacetyl chloride and the like) and chlorinating agents (such as phosphorus oxychloride, thionyl chloride and the like inorganic acid chlorides) and is preferably used in a solvent such as water, dimethylformamide or dioxane at a temperature of 90°–100° C. or under reflux] (Japanese Laid-open Patent Appln. No. 57-116075), and the process wherein 7-alkoxymethylcamptothecins and 7-dialkoxymethyl-camptothecins are obtained by treating 7-hydroxymethylcamptothecin in a lower alcohol (such as methanol, ethanol, n-propanol, isopropanol, n-butanol, isobutanol, t-butanol, n-amyl alcohol, isoamyl alcohol or t-amyl alcohol) or an aralkyl alcohol (such as benzyl alcohol, phenethyl alcohol or phenylpropanol) with an acid (such as sulfuric acid, hydrochloric acid, hydrobromic acid, perchloric acid; Lewis acids, for example, boron trifluoride, aluminum chloride and stannic chloride; trifluoroacetic acid, trichloroacetic acid, benzenesulfonic acid, toluenesulfonic acid or methanesulfonic acid) at a temperature from room temperature to the boiling reflux temperature under such condition that the use of the acid in a catalytic amount or several molar equivalent amount affords a 7-dialkoxymethylcamptothecin exclusively or preferentially, but the use of the acid in a large excess amount, e.g. in a 150–250 molar equivalent amount affords a 7-alkoxymethylcamptothecin exclusively or preferentially (In the event that both of a 7-dialkoxymethylcamptothecin and a 7-alkoxymethylcamptothecin are formed concurrently, both products can be separated and purified by subjecting them to column chromatography on silica gel or high speed fluid chromatography) (Japanese Laid-open Patent Appln. No. 57-116076). However, the types of camptothecin derivatives prepared according to these processes are still limitative.

For further researches on the relation between the substituents in camptothecin derivatives and anti-tumor activity and/or toxicity, therefore, there is still a great demand in this art for developing further new classes of camptothecin derivatives possessing a low level of toxicity while maintaining the inherent anti-tumor activity by chemically modifying 5- and/or 7-substituted camptothecin in a single step without destroying the structure of the rings D and E in the camptothecin molecule.

BRIEF SUMMARY OF THE INVENTION

Accordingly, it is an object of the present invention to provide new 5- and/or 7-substituted camptothecin-1-oxide derivatives.

It is another object of the present invention to provide new 5- and/or 7-substituted camptothecin-1-oxide derivatives which are strong in anti-tumor activity and possess good absorbability in living bodies with very low toxicity.

It is still another object of the present invention to provide processes for the preparation of such new 5- and/or 7-substituted camptothecin-1-oxide derivatives.

Other objects, features and advantages of the present invention will become apparent more fully from the following description.

DETAILED DESCRIPTION OF THE INVENTION

With a view to preparing a new class of camptothecin derivatives possessing the inherent anti-tumor activity with extremely reduced toxicity, the present inventors have made further researches for chemically modifying the 5- and/or 7-substituted camptothecin, paying careful attention to these chemical modifications in order to avoid any destruction of the structure of the rings D and E. As a result of such further work, it has been found that 5- and/or 7-substituted camptothecin-1-oxide derivatives as a new class of camptothecin derivatives can be prepared in a single step without permitting any attack of the rings D and E by treating a 5- and/or 7-substituted camptothecin derivative with a specific oxidizing agent and that the resulting new class of 5- and/or 7-substituted camptothecin-1-oxide derivatives are also provided with anti-tumor activity and extremely reduced toxicity. The present invention has been accomplished on the basis of the above finding.

In accordance with the present invention, there are provided new 5- and/or 7-substituted camptothecin-1-oxide derivatives of the general formula:

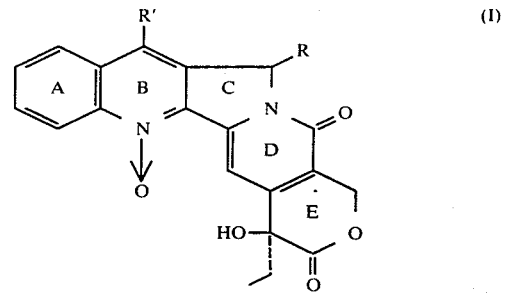

wherein R is a hydrogen atom, an alkyl group, a hydroxyl group, an alkoxy group or an acyloxy group and R' is a hydrogen atom, an alkyl group, an aralkyl group, a hydroxymethyl group, an acyloxymethyl group or a carboxymethyl group, with the proviso that both of R and R' should not be hydrogen atoms.

In the above general formula (I), either one of the substituents R and R' is preferably a hydrogen atom. When R or R' is an alkyl group, it generally has 1–30 carbon atoms. In view of the availability of alkylating reactants, the alkyl group preferably has 1–18 carbom atoms. Illustrative of the alkyl group are, for example, straight or branched chain alkyl groups with 1–30, preferably 1–18 carbon atoms, such as methyl, ethyl, n-propyl, isopropyl, n-butyl, isobutyl, sec-butyl, tert-butyl, n-pentyl, isopentyl, n-hexyl, n-heptyl, n-octyl, 2-ethylhexyl, n-nonyl, n-decyl, undecyl, dodecyl, myristyl, heptadecyl, octadecyl and eicosyl groups. When the alkyl groups are branched, the branched chains may be combined together to form a cycloalkyl group such as cyclopentyl, cyclohexyl or cycloheptyl. When R is an alkoxy group, the alkyl moiety thereof generally corresponds to the aforesaid alkyl group. Preferable examples of the alkoxy group are those derived from straight or branched chain lower alkyl groups with 1–8 carbon atoms, such as methoxy, ethoxy, n-propoxy, isopropoxy, n-butoxy, isobutoxy, tert-butoxy, n-pentyloxy, isopentyloxy, n-hexyloxy, n-heptyloxy, n-octyloxy and 2-ethylhexyloxy groups. When R is an acyloxy group, the alkyl moiety thereof generally corresponds to the aforesaid straight or branched chain alkyl group with 1–18 carbon atoms, such as formyloxy, acetyloxy, propionyloxy, n-butyryloxy, isobutyryloxy, valeryloxy, hexanoyloxy, heptanoyloxy, octanoyloxy, nonanoyloxy, decanoyloxy, undecanoyloxy, dodecanoyloxy, pentadecanoyloxy, hexadecanoyloxy and octadecanoyloxy groups. The acyl group in this case may be derived from aromatic carboxylic acids such as benzoic acid and nucleus-substituted benzoic acids; heterocyclic carboxylic acids such as nicotinic acid; aralkylcarboxylic acids such as phenylacetic acid; and alkyl and aromatic sulfonic acids such as ethanesulfonic acid and nucleus-substituted or -unsubstituted benzenesulfonic acid. Preferable examples of the aralkyl group include benzyl, phenethyl, phenylpropyl and 1-naphthylmethyl groups. When R' is an acyloxymethyl group, the acyl moiety generally corresponds to the aforementioned acyl group. Preferable examples of the acyloxymethyl group include those having the acyl moiety with 1–8 carbon atoms, such as acetoxymethyl, propionyloxymethyl, butyryloxymethyl, valeryloxymethyl, hexanoyloxymethyl, benzoyloxymethyl, phenylacetoxymethyl, nicotinoyloxymethyl, ethanesulfonyloxymethyl and p-toluenesulfonyloxymethyl groups.

Illustrative of the new 5- and/or 7-substituted camptothecin-1-oxide derivatives of the present invention are 5-methylcamptothecin-1-oxide, 5-ethylcamptothecin-1-oxide, 5-propylcamptothecin-1-oxide, 5-butylcamptothecin-1-oxide, 5-octylcamptothecin-1-oxide, 5-hydroxycamptothecin-1-oxide, 5-methoxycamptothecin-1-oxide, 5-ethoxycamptothecin-1-oxide, 5-propoxycamptothecin-1-oxide, 5-butoxycamptothecin-1-oxide, 5-octyloxycamptothecin-1-oxide, 5-acetoxycamptothecin-1-oxide, 5-propionyloxycamptothecin-1-oxide, 5-hexanoyloxycamptothecin-1-oxide, 7-methylcamptothecin-1-oxide, 7-ethylcamptothecin-1-oxide, 7-propylcamptothecin-1-oxide, 7-butylcamptothecin-1-oxide, 7-hexylcamptothecin-1-oxide, 7-octylcamptothecin-1-oxide, 7-benzylcamptothecin-1-oxide, 7-phenylpropylcamptothecin-1-oxide, 7-hydroxymethylcamptothecin-1-oxide, 7-carboxymethylcamptothecin-1-oxide, 7-acetoxymethylcamptothecin-1-oxide, 7-propionyloxymethylcamptothecin-1-oxide, 7-butyryloxymethylcamptothecin-1-oxide, 7-hexanoyloxymethylcamptothecin-1-oxide, and 7-octanoyloxymethylcamptothecin-1-oxide.

In accordance with the present invention, there is also provided a process for the preparation of the new 5- and/or 7-substituted camptothecin-1-oxide derivatives of the general formula:

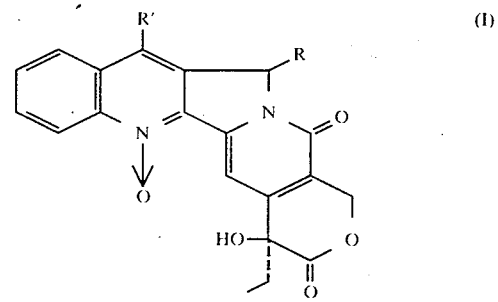

wherein R is a hydrogen atom, an alkyl group, a hydroxyl group, an alkoxy group or an acyloxy group and R' is a hydrogen atom, an alkyl group, an aralkyl group, hydroxymethyl group, an acyloxymethyl group or a carboxymethyl group, characterized by treating a 5- and/or 7-substituted camptothecin derivative of the general formula:

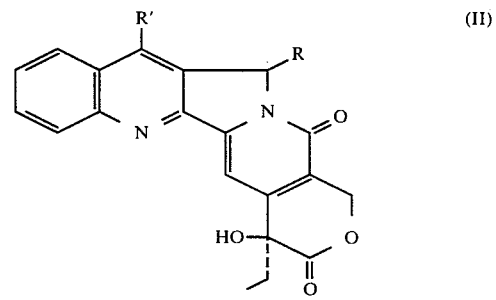

wherein R and R' have the same meanings as given above, with a peroxidant in a liquid vehicle.

The 5- and/or 7-substituted camptothecin derivatives of the general formula (II) used as the starting material are known or can be prepared according to the known prior art processes.

The peroxidant utilizable in the process of this invention for N-oxidation of the ring B (pyridine ring) is selected from the group consisting of hydrogen peroxide, inorganic and organic peracids and salts thereof. Illustrative of the peroxidant are, for example, hydrogen peroxide, peracetic acid, perbenzoic acid, m-chloroperbenzoic acid and a persulfate. The use of hydrogen peroxide is preferable as a higher yield of the product is obtained therewith. The procedure itself for the N-oxidation wherein hydrogen peroxide is used as the peroxidant can be carried out in a manner similar to that described in Mosher et al., Org. Syn. 33, 79(1953), Ochiai et al., J. Pharm. Soc. Japan 71, 1385 (1951) or Boehelheide et al., J. Am. Chem. Soc. 76, 1286 (1954). This procedure can be applied as a new means for N-oxidation of camptothecin itself.

Preferable examples of the liquid vehicle include glacial acetic acid, an aqueous acetic acid solution, hydrocarbons such as benzene and hexane, chlorinated hydrocarbons such as chloroform and methylene chloride, and ethers such as dioxane.

In an embodiment using hydrogen peroxide as the peroxidant, the starting 5- and/or 7-substituted camptothecin derivative is suspended in a small amount of acetic acid or dissolved in a larger amount of acetic acid and then treated under agitation with hydrogen peroxide (usually, about 30% in concentration). The selection of a temperature range from 65° C. to 70° C. is adequate for this reaction. A theoretically needed quantity of hydrogen peroxide is one mol per mol of the starting camptothecin derivative, but the use of a larger excess of hydrogen peroxide (about 30 molar proportion) for the starting camptothecin derivative is preferable. Under such conditions, the N-oxidation of the starting compound is completed normally within 4 hours.

In another embodiment using a peracid as the peroxidant, the starting 5- and/or 7-substituted camptothecin derivative is treated, for example, with peracetic acid (usually, 40% in concentration) and a salt of acetic acid such as sodium acetate or with perbenzoic acid in benzene under conditions similar to those mentioned above. It is possible to use m-chloroperbenzoic acid as the peroxidant in an organic liquid vehicle such as the above mentioned chlorinated hydrocarbons or ethers. It is also possible to use a persulfate as the peroxidant under the similar conditions. The N-oxidation reaction per se with these peracids and a persulfate is known and can be carried out, for example, according to the method as described in Herz et al., J. Am. Chem. Soc. 76, 4184 (1954) and Matsumura, J. Chem. Soc. 74, 446 (1953).

The resultant N-oxide product can be isolated in a highly pure form, for example, concentrating the reaction mixture under reduced pressure to a volume of about 1/5–1/10, diluting the concentrate with a large excess of ice water, collecting the resultant N-oxide precipitated as needle crystals by filtration, and drying the crystals under subatmospheric pressure. The products thus obtained can be used as such without further purification as active ingredients for medicaments or as intermediate products for preparing other useful products.

The present invention is of particular significance in developing a new class of camptothecin derivatives useful as anti-tumor agents possessing anti-tumor activity with slight toxicity and as intermediate products for preparing other useful products as well as a process for preparing these new camptothecin derivatives in a simple industrially advantageous operation.

The present invention will now be illustrated in more detail by way of examples. In these examples, percentage is by weight unless otherwise indicated.

EXAMPLE 1

(Preparation of camptothecin-1-oxide)

Camptothecin (1.04 g, 3 m-mol) is suspended in acetic acid (100 ml). To this suspension is added 30% hydrogen peroxide (15 ml), and the mixture is stirred for 3 hours at 60°–70° C. The resultant reaction mixture is concentrated under reduced pressure to a volume of about 35 ml and the concentrate is then poured into ice water (500 ml). The precipitated yellowish orange needle crystals are collected by filtration, washed with water and then with methanol and dried under reduced pressure whereby 866 mg (yield: 90.6%) of camptothecin-1-oxide is obtained. M.P. 254° C. (dec.)

EXAMPLE 2

(Preparation of 5-methylcamptothecin-1-oxide)

5-Methylcamptothecin (362 mg, 1 m-mol) is dissolved in acetic acid (25 ml). To this solution is added 30% hydrogen peroxide (2.5 ml, 0.0245 mol), and the mixture is warmed for 3 hours at 65°–70° C. The reaction mixture is concentrated under reduced pressure to a volume of about one fifth and diluted with ice water (250 ml). The precipitated yellowish orange needle crystals are collected by filtration and dried at 60° C. for 6 hours under reduced pressure whereby 234 mg (yield: 62.0%) of 5-methylcamptothecin-1-oxide is obtained. M.P. 226° C.— (dec.) MS: m/e 378 [M+] ($C_{21}H_{18}N_2O_5=378$).

EXAMPLE 3

(Preparation of 5-methoxycamptothecin-1-oxide)

5-Methoxycamptothecin (190 mg, 0.5 m-mol) is dissolved in acetic acid (15 ml). To this solution is added 30% hydrogen peroxide (1.25 ml, 0.0125 mol), and the mixture is stirred for 3 hours at 65°–70° C. The reaction mixture is concentrated under reduced pressure to a volume of about one fourth and diluted with ice water (200 ml). The precipitated yellowish orange needle crystals are collected by filtration and then dried under reduced pressure for 6 hours at 60° C. whereby 145 mg (yield: 73.6%) of 5-methoxycamptothecin-1-oxide is obtained. M.P. 208° C.— (dec.)

NMR (in CDCl$_3$): 1.03 (3H, t, J=7 Hz), 1.92 (2H, q, J=7 Hz), 3.51, 3.66 (1.5H×2, s, s), 5.30 (1H, d, J=16 Hz), 5.59 (1H, d, J=16 Hz), 6.73, 6.85 (0.5H×2, s, s), 7.72–8.01 (4H, m), 8.24 (1H, s), 8.76 (1H, m).

MS: m/e 394 [M+] ($C_{21}H_{18}N_2O_6=394$).

EXAMPLE 4

Preparation of 7-ethylcamptothecin-1-oxide)

7-Ethylcamptothecin (1.00 g, 2.65 m-mol) is dissolved in acetic acid (300 ml). To this solution is added 30% hydrogen peroxide (7.5 ml, 0.0736 mol), and the mixture is stirred for 3 hours at 65°–70° C. The reaction mixture is concentrated under reduced pressure to a volume of about one fourth and diluted with ice water (500 ml). The precipitated yellowish orange needle crystals are collected by filtration and dried for 6 hours at 60° C. under reduced pressure whereby 808 mg (yield: 77.7%) of 7-ethylcamptothecin-1-oxide is obtained. M.P. 255° C.— (dec.).

NMR (in DMSO-d$_6$): 0.87 (3H, t, J=7 Hz), 1.28 (3H, t, J=7 Hz), 1.84 (2H, q, J=7 Hz), 3.10 (2H, q, J=7 Hz), 5.26 (2H, s), 5.36 (2H, s), 6.24 (1H, s, D$_2$O-exchangeable), 7.80 (3H, m), 8.10 (1H, s), 8.35 (1H, m).

MS: m/e 392 [M+] ($C_{22}H_{20}N_2O_5=392$).

EXAMPLE 5

(Preparation of 7-propylcamptothecin-1-oxide)

7-Propylcamptothecin (390 mg, 1 m-mol) is dissolved in acetic acid (55 ml). To this solution is added 30% hydrogen peroxide (3 ml, 0.0294 mol), and the mixture is stirred for 4 hours at 65°–70° C. The reaction mixture is concentrated under reduced pressure to a volume of about 10 ml and diluted with ice water (250 ml). The precipitated yellowish orange needle crystals are collected by filtration and dried for 6 hours at 60° C. under reduced pressure whereby 278 mg (yield: 68.4%) of 7-propylcamptothecin-1-oxide is obtained. M.P. 238° C.— (dec.) MS: m/e 406 [M+] ($C_{23}H_{22}N_2O_5=406$).

EXAMPLE 6

(Preparation of 7-benzylcamptothecin-1-oxide)

7-Benzylcamptothecin (250 mg, 0.570 m-mol) is dissolved in acetic acid (50 ml). To this solution is added 30% hydrogen peroxide (2 ml, 0.0196 mol), and the mixture is stirred for 3 hours at 65°–70° C. The reaction mixture is concentrated under reduced pressure to a volume of about 10 ml and then diluted with ice water (250 ml). The precipitated yellowish orange needle crystals are collected by filtration and dried for 6 hours at 60° C. under reduced pressure whereby 164 mg (yield: 63.5%) of 7-benzylcamptothecin-1-oxide is obtained. M.P. 220° C.— (dec.).

NMR (in CDCl$_3$): 1.09 (3H, t, J=7.5 Hz), 1.87 (2H, q, J=7.5 Hz), 4.48 (2H, s), 5.16 (2H, s), 5.20 (1H, d, J=16 Hz), 5.64 (1H, s, J=16 Hz), 7.05–8.12 (8H, m), 8.32 (1H, s), 8.80 (1H, m).

MS: m/e 454 [M+] ($C_{27}H_{22}N_2O_5$=454).

EXAMPLE 7

(Preparation of 7-acetoxymethylcamptothecin-1-oxide)

7-Acetoxymethylcamptothecin (1.0 g, 2.38 m-mol) is dissolved in acetic acid (150 ml). To this solution is added 30% hydrogen peroxide (10 ml, 0.0981 mol), and the mixture is stirred for 3.5 hours at 65°–70° C. The reaction mixture is concentrated under reduced pressure to a volume of about 50 ml, diluted with ice water (350 ml) and extracted with chloroform (300 ml×3). The chloroform phase is washed with a 7% aqueous solution of sodium hydrogen carbonate, dried over magnesium sulfate and dried until dryness under reduced pressure. The residue is purified by reprecipitation with chloroform-n-hexane whereby 679 mg (yield: 65.9%) of 7-acetoxymethylcamptothecin-1-oxide is obtained as yellow needle crystals. M.P. 250° C.— (dec.)

NMR (in DMSO-d$_6$): 0.87 (3H, t, J=7 Hz), 1.83 (2H, q, J=7 Hz), 2.05 (3H, s), 5.42 (4H, br s), 5.61 (2H, s), 6.42 (1H, s, D$_2$O-exchangeable), 7.80 (2H, m), 7.91 (1H, s), 8.20 (1H, m), 8.63 (1H, m).

MS: m/e 436 [M+] ($C_{23}H_{20}N_2O_7$=436).

EXAMPLE 8

(Preparation of 7-hydroxymethylcamptothecin-1-oxide)

7-hydroxymethylcamptothecin (300 mg, 0.794 m-mol) is suspended in glacial acetic acid (70 ml). To this suspension is added 30% hydrogen peroxide (30 ml), and the mixture is stirred for one hour at 70°–80° C. 30% Hydrogen peroxide (20 ml) is added and the mixture is further stirred for 1.5 hours at 70°–80° C. The reaction mixture is concentrated under reduced pressure to a volume of 40 ml. Ice water (60 ml) is added to the concentrate and the mixture is allowed to stand for 12 hours. The precipitated yellow crystals are collected by filtration and dried under reduced pressure whereby 142 mg (yield: 45.4%) of the objective compound is obtained as yellow needle crystals. M.P. 255°–260° C. (dec.)

IR $\nu_{max}^{KBr}$cm$^{-1}$: 3400, 2940, 1755, 1650, 1600, 1460, 1160, 1100, 765.

What is claimed is:

1. A 5- or 7-substituted camptothecin-1-oxide derivative of the formula:

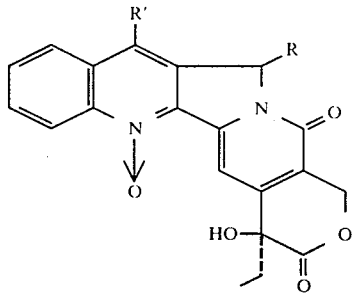

wherein R is a hydrogen atom, a straight or branched C$_1$–C$_{30}$ alkyl group, a C$_5$–C$_7$ cycloalkyl group, a hydroxyl group, a C$_1$–C$_{30}$ alkoxy group or a C$_1$–C$_{18}$ acyloxy group and R$^1$ is a hydrogen atom, a C$_1$–C$_{30}$ alkyl group, a phenylalkyl group, a naphthylalkyl group, a hydroxymethyl group, a C$_1$–C$_{18}$ acyloxymethyl group or a carboxymethyl group, with the proviso that both R and R$^1$ are not hydrogen.

2. A 5-alkylcamptothecin-1-oxide having 1 to 18 carbon atoms in the alkyl group thereof.

3. A 5-alkoxycamptothecin-1-oxide having 1 to 18 carbon atoms in the alkoxy group thereof.

4. A 7-alkylcamptothecin-1-oxide having 1 to 18 carbon atoms in the alkyl group thereof.

5. A 7-aralkylcamptothecin-1-oxide derivative wherein the aralkyl group is selected from the group consisting of benzyl, phenethyl, phenylpropyl and 1-naphthylmethyl.

6. A 7-acyloxymethylcamptothecin-1-oxide oxide having 1 to 18 carbon atoms in the alkyl group thereof.

7. 7-Hydroxymethylcamptothecin-1-oxide.

8. A 5- or 7-substituted camptothecin-1-oxide derivative as in claim 1, wherein the alkyl group contains from 1 to 18 carbon atoms, the alkoxy group contains from 1 to 8 carbon atoms and the acyl group contains from 1 to 8 carbon atoms.

* * * * *